United States Patent [19]

Seyl

[11] 4,102,769

[45] Jul. 25, 1978

[54] CORROSION PROBE

[76] Inventor: Robert G. Seyl, 1123 Mulford St., Evanston, Ill. 60202

[21] Appl. No.: 785,865

[22] Filed: Apr. 7, 1977

[51] Int. Cl.² .................. G01N 27/30; G01N 27/08
[52] U.S. Cl. ............................... 204/195 C; 73/86; 204/286; 324/65 CR
[58] Field of Search ............... 204/1 C, 195 C, 286; 324/65 CR; 73/86; 23/253 C

[56] References Cited

U.S. PATENT DOCUMENTS

| | | | |
|---|---|---|---|
| 3,364,422 | 1/1968 | Heuze | 324/71 |
| 3,418,848 | 12/1968 | Schaschl | 73/86 |
| 3,486,996 | 12/1969 | Annand | 204/195 C |
| 3,616,415 | 10/1971 | Watson et al. | 204/195 C |
| 3,772,178 | 11/1973 | Wilson | 204/195 C |
| 3,788,962 | 1/1974 | Frenck | 204/195 C |
| 3,948,744 | 4/1976 | Cushing | 204/195 C |

OTHER PUBLICATIONS

R. L. Geisert et al. "A Versatile Polarization Cell System", *Corrosion*, vol. 32, pp. 407–410 (1976).

*Primary Examiner*—Aaron Weisstuch
*Attorney, Agent, or Firm*—McWilliams & Mann

[57] ABSTRACT

An electrode probe for accurate corrosion current measurement of metals in ionically conducting liquids. Electrode, and insulator to probe holder, are cylindrical surfaces of the same diameter, to combine minimum disturbance of liquid flow past electrode surfaces with substantially uniform density of current passed between the electrodes. Elastic outside shields form water-repellent interfaces that substantially exclude crevice corrosion and define exposed electrode length and area with precision.

7 Claims, 5 Drawing Figures

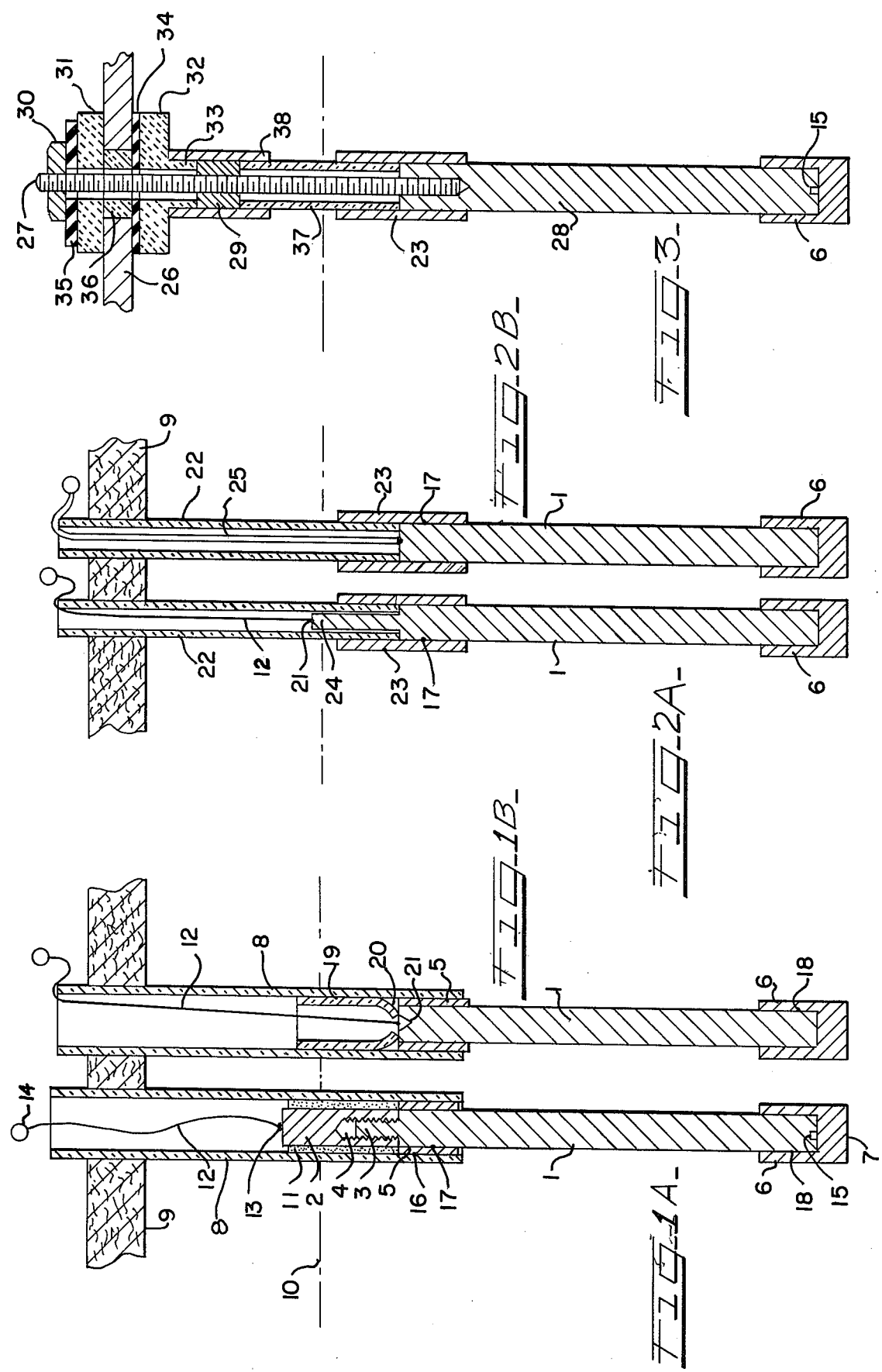

CORROSION PROBE

BACKGROUND AND SUMMARY OF THE INVENTION

This invention relates to electrode probes for measuring corrosion currents of metals immersed in ionically conducting liquids.

Corrosion current measurements made in accordance with my U.S. Pat. No. 3,694,324 require the use of at least three electrodes. In one alternative, two duplicated measured electrodes and one electrode operated as an anode are required. In another alternative, one measured, one reference, and one opposed electrode are required.

In practice, each electrode with its lead wire is held in an electrical insulator, the combination being termed an electrode assembly. A plurality of electrode assemblies are positioned and held in selected spacial relationship by securing them to an electrode holder. The electrode holder can vary in form according to how it is in turn held in selected spacial relationship to the liquid corrosive. The simplest form of electrode holder is one supported by the top edges of the container holding the liquid corrosive. More complicated forms of electrode holders are used for holding electrodes in tanks and pipes, and the combination of electrodes and electrode holder has been termed an electrode probe by the manufacturer and by users in the field.

An early form of electrode probe is illustrated in FIG. 12 of said above patent. A plurality of cylindrical electrodes of the corroding metal are secured at one end in selected spaced relationship and with their major axes parallel, by an insulator, such as an epoxy plastic, that is cast into a metal cylinder, frequently of stainless steel.

This form of probe has proven to be very useful in the control of corrosion occurring in the field, through the monitoring of corrosion rate measurements made at selected spaced intervals of time. Since such monitoring generally requires only relative corrosion current measurement, it is possible to reuse the probe occasionally after cleaning the electrodes.

This probe has also been elaborated in the form of removable electrodes, which permits weighing of the electrodes before and after the observed duration of the corrosion, and which enables repeated use of the electrode holder to economic advantage. The electrodes are screwed into the holder, and the bolt threads can alternatively be on the end of the holder. The end of the electrode is sealed to the insulator by means of an elastic washer fitting over the bolt member.

A higher order of measurement performance is required from the probe when accurate corrosion rate measurements are applied to research and development applications evaluating the single and combined effects of factors of corrosion system performance, such as metal composition, corrosive liquid composition, corrosive environment such as temperature and flow rate, the use of inhibitors, and the possible presence of accelerators.

One limitation to the above form of probe is the metal cylinder into which the insulator is cast. With the finite volume of corrosive liquid generally used in the laboratory, the additional metal area introduced by the cylinder can alter the performance of the corrosive with the passage of time. If the composition of the metal cylinder differs from that of the electrodes, its corrosion products can cause a further disturbance.

Other limitations originate from the use of a single insulator body of diameter several times that of a single electrode, with the electrode surfaces terminating into the cross-sectional area of the insulator body. When the corrosive solution flows past the electrodes, the uniformity of flow paths is substantially disturbed by the insulator body.

Uniformity of current flow is disturbed by the combined effects of an insulator body shield at the top of the electrodes and no shield at the bottom tips of the electrodes. Conditions favoring uniform current flow to and from electrode surfaces are essential to producing corrosion current-time relationships that accurately measure metal losses when correlated with weighed metal losses. These conditions become more critical as the ionic conductor resistivity increases into the region of make-up water and passes into the range of distilled water.

The washer of the removable electrode probe that seals the electrode to the insulator is seated on a shoulder machined on the electrode in a plane perpendicular to the major axis of the electrode. Exposed electrode surface terminates at a 90° angle to the washer, which favors the development of crevice corrosion along the electrode surface in contact with said washer. Such corrosion is objectionable because it is shielded from corrosion current measurement, and because it diminishes the contact area relied upon to keep the electrode in a tightly screwed-in position in the presence of vibration.

The above limitations recognized in these probes are in part corrected in this invention through mechanical design, but the substantial elimination of crevice corrosion did not initially appear to be possible.

Crevice corrosion occurs in the presence of an accelerator such as dissolved oxygen. When a small area of the total exposed metal surface is shielded from the cathodic depolarizing action of the dissolved oxygen, it operates as an anode area with corrosion rate accelerated through short-circuit coupling to the large exposed surface area undergoing cathodic depolarization. The finding that crevice corrosion was serious when the electrode surface was sealed to insulator surface with beeswax, was understandable through recognition that anodic corrosion products could easily deform the wax and increase the anodic area. Sealing the electrode surface to the insulator surface with an epoxy resin cured in position with its admixed hardener, to form one of the strongest known adhesive bonds, diminished but did not substantially eliminate the crevice corrosion.

The concept of a seal in the form of an elastic material pressed to the metal surface through tension forces, was tried in the form of rubber tubing stretched over cylindrical electrode surface. This concept became workable when the interface between the shield and metal was made water-repellent by a coating of Vaseline. Later, a silicone grease, inert to rubber and noted for its strong water repellency and good temperature resistance produced more reliable results, and promotes an easily removable form of shielding.

OBJECTS

The objects of this invention include alternative forms of electrode probe for measuring corrosion currents that incorporate the following features:

1. Metal surface exposed to the corrosive liquid is only that of the electrode surface;

2. Crevice corrosion at the boundaries between electrode surfaces and insulator surfaces is substantially eliminated;

3. Paths of corrosive liquid flow past the electrode surfaces undergo minimum disturbance;

4. Density of current flow to or from the electrode surfaces is substantially uniform;

5. The seal of the electrode to its insulator retains electrode position and electrical contact in the presence of mechanical vibration;

6. Area of exposed electrode surface is adjustable to selected values with precision.

BRIEF DESCRIPTION OF THE DRAWINGS

FIG. 1-A shows the cross-section of an electrode assembly in part accomplishing objectives of this invention but which requires careful material selection for elevated temperature operation;

FIG. 1-B shows a simplification not restricted to temperatures at atmospheric pressures;

FIGS. 1-A and 1-B together illustrate electrode assembly spacing in a corrosion probe;

FIG. 2-A shows in cross-section an improvement over the construction of FIG. 1-B;

FIG. 2-B shows a simplification of FIG. 2-A;

FIGS. 2-A and 2-B together illustrate electrode assembly spacing in a corrosion probe;

FIG. 3 shows the cross-section of an electrode assembly for operation above boiling temperature and above atmospheric pressure.

DESCRIPTION OF THE PREFERRED EMBODIMENTS

One form of electrode assembly incorporating some of the features of this invention is shown in cross-section in FIG. 1-A. Electrode 1 is in the form of a metal cylinder of the metal to undergo corrosion. By way of example, but not by way of limitation, its diameter is 4.0 mm., and its total cylindrical length is 46 mm. Exposed length of 32 mm. produces the exposed area of 4.02 sq. cm. A receiving cylinder 2, is of substantially the same diameter as the electrode, and is of a metal selected to meet requirements of coefficient of thermal expansion, ease of machinability, and corrosion resistance. Electrode 1 is removably secured by threaded bolt 3 and tapped hole 4, of size such as 2–56. In one form, the bolt is machined from the receiving cylinder stock, and the electrode is drilled and tapped.

Top electrode shield 5 and bottom electrode shield 6 are made of shield tubing of corrosion resistant and electrically insulating material, of internal diameter less than the diameter of said electrode, and of elasticity permitting the placement of said shield tubing over said electrode. For example, tubing of a variety of materials can be used, including natural and synthetic rubbers, and plastics such as polyvinyls. The length of these sections of shield tubing is generally at least twice the electrode diameter. One end of shield 6 is closed by a corrosion resistant, electrically insulating material 7, which can be of the same material as the shield tubing.

An electrode mounting tube 8, of a corrosion resistant and electrically insulating material, such as glass, is selected of internal diameter to fit closely over the top electrode shield 5. This mounting tube is fixed in spacial relationship to other electrodes by passing through a hole in electrode holder 9, where it can be permanently cemented or secured for effective length adjustment by means such as a set screw threaded into said electrode holder. The length of said mounting tube is determined by two factors. When the corroding liquid has significant ohmic resistance, the top of the exposed electrode surface should be below the liquid surface level 10, by a distance of at least one half of the exposed electrode length, to avoid interference with paths of current conduction within said liquid corrosive.

Electrode holder 9 is positioned and secured in fixed relationship to the container, or is held by a clamp separate from said container, or is attachable to a wall of said container. Additional mounting tube length must be enough to pass said tubing through said electrode holder. Receiving cylinder 2, is permanently attached to mounting tube 8 by a cementing material 11. A lead wire 12, is connected to receiving cylinder 2 at point 13, and extends to terminal point 14, shown diagramatically.

In operation, electrode 1 is made from rod stock of selected composition and heat treatment, and turned on a lathe to a specified diameter. Additional machining includes the threading or tapping for the threaded connection 3, and the cutting of a screw driver slot 15 at the bottom end of the electrode. Top shield 5 is lightly coated on the outside with a water-repellent and inert grease, such as a silicone grease, and is inserted into the bottom of electrode mounting tube 8, to form a water-repellent interface 16. A light coat of this grease is then applied to the inside of said shield. The electrode is then inserted and screwed tight by means of screw driver slot 15, to form water-repellent interface 17. It is found that air is expelled consequent to the elasticity of shield 5, while the progress of the electrode into this shield prevents displacement of the shield from electrode mounting tube 8. The inside of bottom shield 6 is coated lightly with said grease, and the shield is pushed over the lower end of said electrode to form water-repellent interface 18. It is found that air is expelled, and the shield is then held in position by vacuum action. Crevice corrosion is avoided by the combined actions of elastic shielding material fitting snugly over the electrode surface, and a water-repellent interface between said shield and electrode surface produced by said grease.

The electrode assembly of FIG. 1-A operates well at room temperature, but elevated temperature presents the problem of matching the coefficients of thermal expansion of parts 2, 11, and 8, to avoid breakage of tube 8. The machining required for part 2 adds to cost. These limitations are overcome in the electrode assembly of FIG. 1-B.

FIG. 1-B shows in cross-section a simplified and less expensive means for securing electrode 1 to electrode mounting tube 8. Glass tubing of outside diameter closely fitting the inside diameter of glass tube 8 is heated at one end to reduce its end diameter to an extent which still allows lead wire 12 to be subsequently passed therethrough. The tubing is then broken about two centimeters from said end, and the section 19 is placed within tube 8 with the small diameter end down. It is positioned so that the small diameter end is at a depth substantially equal to that of the lower end of receiving cylinder 2 of FIG. 1-A, and then fused to the inner wall of tube 8, as shown at 19. The end of reduced diameter 20, operates as a shoulder against which electrode 1 can be positioned. Top electrode shield 5 can be sealed to electrode mounting tube 8 with a cement such as silicone rubber cement. Lead wire 12 is soldered to electrode 1 at the tailstock centering hole 21, made before turning the electrode on a lathe. The inside wall of top electrode shield 5 is lightly coated with silicone grease, lead wire 12 is inserted through the reduced diameter at 20, and the electrode is positioned against the shoulder formed at 20. As a precaution to assure retention of the electrode, lead wire 12 can be bent over the top of tube 8 as shown.

FIGS. 1-A and 1-B together, show the electrode assemblies mounted in electrode holder 9 to form a probe, with the electrode mounting tubes 8 separated by a distance equal to the 4.0 mm. diameter of electrode 1. The only metal surface exposed to the corrosive is that of the electrodes. The top electrode shield tends to hold the electrode in its secured positioned. The use of a separate mounting tube for each electrode improves uniformity of liquid flow past the electrodes, and contributes toward the attainment of uniform density of current flowed to or from the electrodes. Crevice corrosion is substantially eliminated.

FIG. 2-A shows in cross-section an electrode assembly of further simplified design, that is also accompanied by significant operational advantages. It is the preferred embodiment for operation with high flow rates at atmospheric pressure. Electrode mounting tube 22 is of external diameter selected to be substantially equal to the external diameter of electrode 1. Top electrode shield 23 is extended in length to fit over both mounting tube 22 and electrode 1, after application of a thin coat of silicone grease to its inner wall to form water-repellent interface 17. The lathe turning of electrode 1 is elaborated by the additional turning of a tab cylinder 24, of about one centimeter length, and of diameter slightly smaller than the internal diameter of tube 22. The function of this tab is to reinforce the holding of the major axis of the electrode in alignment with the major axis of the mounting tube. Lead wire 12 is soldered to tab 24 at the centering hole 21.

Constructional advantages of FIG. 2-A include the requirement of only a single electrode mounting tube for electrode positioning, with external diameter requirement easily met by the comparatively wide tolerance within which glass tubing is received. Hydraulic pressure of the liquid corrosive operates perpendicular to the outside surface of shield 23 to further the sealing action of interface 17. Exposed length of electrode surface can be adjusted with precision by carefully lowering the position of shield 23 after electrode securement by lead wire 12 and while measuring the distance between the lower end of shield 23 and the upper end of shield 6.

The electrode assembly shown in cross-section in FIG. 2-B is the preferred embodiment for operation with low flow rates at atmospheric pressure. The FIG. 2-B structure eliminates the tab electrode member 24 of FIG. 2-A, and substantially accomplishes the function of this tab through the use of heavy lead wire 25. Copper wire of #18 gauge, 0.040 inch diameter, generally accomplishes this objective.

FIGS. 2-A and 2-B together, show the electrode assemblies mounted in electrode holder 9 to form a probe. The electrodes of 4.0 mm. diameter are separated by a 9 mm. spacing between their major axes. It can be observed from inspection that the electrode mounting tubes of same diameter as the electrodes introduce substantially no disturbance of corrosive solution flow around the electrodes, particularly when corrosive solution level is above the minimum requirement shown in the figures.

An additional consideration relates to minimum spacing between electrode surfaces. This spacing generally is made no smaller than the diameter of the electrode, to permit solution flow between the electrodes and to allow for the possible build-up of corrosion products. Minimum spacing is desirable, because increase of spacing increases the space required by major conduction paths through the ionically conducting liquid in both horizontal and vertical planes. In FIGS. 1-A and 1-B, minimum spacing was determined by separating electrode mounting tubes 8 by the 4.0 mm. electrode diameter, and the major axes of the electrodes are consequently separated by 12 mm. The smaller separation of 9 mm. in FIGS. 2-A and 2-B decreases the minimum required separation distance between electrode axis and any non-conducting liquid-containing boundary such as the glass wall of a container for the liquid, as well as the surface of the liquid.

FIG. 3 illustrates in cross-section an electrode assembly for use when the corrosive environment includes pressure greater than atmospheric. It is the preferred embodiment for operation with high flow rates and with pressure greater than atmospheric. In such applications, the corrosive liquid is usually held in a suitable strong metal container, and electrode holder 26 is regarded to be of metal. In this electrode assembly electrical connection from the electrode to the outside connection terminal is in the form of a threaded bolt 27. Bolt size of 6–32 is satisfactory because this diameter enables operation with an electrode diameter of 5.0 mm., the use of steel provides necessary strength, and the bolt is on the market with zinc plating as stock in two foot lengths. After electrode 28 is turned and polished on the lathe, it is drilled to a depth of 3/16 inch, and tapped. Bolt 27 is held in position by threaded collar 29 of the same outside diameter as the electrode, and by nut 30. The insulating seal to electrode holder 26 includes insulators 31 and 32 of a strong temperature-resistant material such as porcelain. Insulator 32 includes a lower cylindrical portion 33, of the same outside diameter as electrode 28. Inside washer 34, of some elasticity, produces the inside seal to electrode holder 26. Outside washer 35 distributes the force applied from nut 30. Bolt 27 is insulated from contact with electrode holder 26 by the section of insulating tubing 36, of length slightly less than the thickness of 26.

In assembly, bolt 27 is secured in position to produce the selected separation distance between the lower surface of holder 26 and the top of electrode 28. The length of electrode mounting tube 37 is cut to a slightly shorter length than the distance from collar 29 to electrode 28, to avoid imposing any compression force when the electrode is finally tightened. Electrode mounting shield 38 is of the same material and properties as top electrode shield 23 and bottom electrode shield 6, is also operated with the water-repellent interface, and is applied first to hold electrode mounting tube 37 in position before the electrode is screwed to bolt 27 and tightened through use of screw driver slot 15.

To a limited extent, heat shrinkable plastic tubing, used in the electronic and other industries, is an alternative to electrode shielding with elastic tubing and a water-repellent silicone grease. The elasticity of such tubing is developed by the shrinking temperature, said to range from 75° to 275° F, but upon cooling, little elasticity persists. Although the plastic is itself water-repellent, it is not regarded to operate reliably without the silicone water-repellent. Lengthwise shrinkage also occurs, and interferes with the precision adjustment of exposed electrode length.

The electrodes of FIGS. 1-A and 3 are removable by unscrewing for final weighing. Weighings of the electrodes of FIGS. 1-B and 2-A and 2-B, are made with the lead wire attached to the electrode.

The effectiveness in attaining good uniformity of current density in corrosion current measurement is evidenced from the accuracy with which the measured current-time relationship, when integrated to a weight-time relationship through Faraday's Law of Electrolysis, measures metal loss. The effect of non-uniform current density is to introduce a negative error in measured value of corrosion current.

In general, weighed metal losses measured on duplicated electrodes can be in agreement within an average of about ±5 percent. With good uniformity of current density, it has been found that even with corrosive liquids of high ohmic resistivity, accelerated by dissolved oxygen, the form of electrode probe disclosed in FIGS. 2 and 3 can produce corrosion current measurement of about ±7 percent accuracy, when operated with circuitry correcting for the ionic conductor resistance.

I claim:

1. An electrode probe for positioning metal electrodes within an ionically conducting liquid comprising:
   an electrode of a metal to undergo corrosion, having a cylindrical electrode surface of selected diameter and length;
   an electrode mounting tube selected from a material that is corrosion resistant and electrically insulating, said tube positioned with the major axis thereof in alignment with the major axis of said electrode and with the bottom end thereof against the top end of said cylindrical electrode surface such that the length of said tube determines the depth of immersion of said electrode in said ionically conducting liquid; said tube of a diameter substantially equal to the diameter of said electrode for minimum disturbance of liquid flow past said electrodes and surfaces thereof;
   electrode holder means for securing said electrode mounting tube in a manner which permits positioning of the electrode for immersion in said ionically conducting liquid;
   an electrical conductor in electrical contact with said electrode and extending through said electrode mounting tube and said electrode holder to an electrical terminal;
   top electrode shield means comprising a selected length of tubing of a corrosion resistant and electrically insulating material, said tubing positioned over the bottom end of said electrode mounting tube and over the top end of said electrode surface, said tubing having sufficient elasticity to hold said tubing firmly against the electrode and electrode mounting tube surfaces after adjustment of position thereabout;
   bottom electrode shield means comprising a selected length of tubing of corrosion resistant and electrically insulating material, a top end of said tubing positioned over the bottom end of said electrode, said tubing having sufficient elasticity to hold said tubing firmly against the electrode surfaces after placement thereover, means for closing a bottom end of said tubing with a corrosion resistant and electrically insulating material;
   a water-repellent inert viscous material applied in a thin film to an interface area between said bottom electrode shield means and the bottom end of said electrode and to another interface area between said top electrode shield means, said electrode surface and said electrode mounting tube, thereby substantially preventing crevice corrosion;
   said top and bottom electrode shield means thereby accurately defining exposed electrode length and area and further providing substantially uniform current density between said electrodes; and
   means for securing and releasing said electrode for weight measurement.

2. The electrode probe of claim 1, in which said tubing for said top and bottom shield means is of internal diameter smaller than the diameter of said electrode, and is of elasticity permitting the placement of said tubing over said electrode.

3. The electrode probe of claim 1, in which said tubing for said top and bottom shield means is in the form of heat shrinkable plastic tubing of internal diameter permitting placement of said tubing over said electrode, and in which said tubing is then heated to contract it in firm contact with electrode and electrode mounting tube surfaces.

4. The electrode probe of claim 1, in which said electrical conductor is in the form of a lead wire connected to the top end of said electrode and passing through said electrode mounting tube and said electrode holder to a point of removable securement above the top surface of said electrode holder.

5. The electrode probe of claim 1, in which said electrical conductor is in the form of a threaded bolt threading into the top end of said electrode and passing through said mounting tube and said electrode holder, with said bolt secured to the bottom side of said electrode holder by a threaded collar of external diameter equal to that of said electrode and covered by a section of said tubing, and with said bolt secured to the top side of said electrode holder by a nut.

6. The electrode probe of claim 1, in which the major axis of said electrode is maintained in alignment with the major axis of said electrode mounting tube by a cylindrical tab member on the top end of said electrode, said tab member having an external diameter slightly less than the internal diameter of said electrode mounting tube thereby permitting said tab member to be inserted into said electrode mounting tube.

7. The electrode probe of claim 1, in which the major axis of said electrode is maintained in alignment with the major axis of said mounting tube by the flexural resistance of the lead wire from said electrode that passes through said mounting tube.

* * * * *